United States Patent
Habbecke et al.

(10) Patent No.: US 11,657,087 B2
(45) Date of Patent: May 23, 2023

(54) SURGICAL VIDEO RETRIEVAL BASED ON PREOPERATIVE IMAGES

(71) Applicant: Verily Life Sciences LLC, South San Francisco, CA (US)

(72) Inventors: Martin Habbecke, Palo Alto, CA (US); Joëlle K. Barral, Mountain View, CA (US); Lin Yang, Sunnyvale, CA (US); Xing Jin, San Jose, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 1019 days.

(21) Appl. No.: 16/299,965

(22) Filed: Mar. 12, 2019

(65) Prior Publication Data

US 2019/0286652 A1    Sep. 19, 2019

Related U.S. Application Data

(60) Provisional application No. 62/644,737, filed on Mar. 19, 2018.

(51) Int. Cl.
*G06F 16/783* (2019.01)
*G06F 16/71* (2019.01)
(Continued)

(52) U.S. Cl.
CPC .......... *G06F 16/7837* (2019.01); *A61B 34/10* (2016.02); *A61B 34/20* (2016.02);
(Continued)

(58) Field of Classification Search
CPC ........ G16H 10/60; G16H 20/40; G16H 30/20; G16H 30/40; G16H 50/70; G06V 10/70;
(Continued)

(56) References Cited

U.S. PATENT DOCUMENTS 7,570,790 B2    8/2009    Tsujii et al.
9,489,455 B2    11/2016   Pereira et al.
(Continued)

FOREIGN PATENT DOCUMENTS

JP    2007275408 A    10/2007
WO   2009/113102 A2   9/2009
WO   2016/200887 A1   12/2016

OTHER PUBLICATIONS

Dou et al., "3D Deeply Supervised Network for Automatic Liver Segmentation from CT Volumes," 8 pages.
(Continued)

*Primary Examiner* — Manuchehr Rahmjoo
(74) *Attorney, Agent, or Firm* — Christensen O'Connor Johnson Kindness PLLC

(57) ABSTRACT

A system includes a display, and a database including surgical videos, images of organs in a human body obtained from a medical imaging device, and images of disease in a human body obtained from the medical imaging device. A controller including a processor is coupled to memory, the database, and the display, and the memory stores information that when executed by the processor causes the system to perform operations. For example, the processor may determine first organ information from the images of the organs, and first disease information from the images of the disease. The processor my calculate a similarity score between the first organ information and the first disease information and second disease information and second organ information indexed to the surgical videos. The processor selects one or more of the surgical videos based on the similarity score, and displays the surgical videos on the display.

23 Claims, 6 Drawing Sheets

(51) Int. Cl.

| | | |
|---|---|---|
| *A61B 90/00* | (2016.01) | |
| *G06N 20/00* | (2019.01) | |
| *G16H 10/60* | (2018.01) | |
| *A61B 34/20* | (2016.01) | |
| *G16H 30/20* | (2018.01) | |
| *G16H 20/40* | (2018.01) | |
| *A61B 34/10* | (2016.01) | |
| *G09B 23/28* | (2006.01) | |
| *G06V 10/70* | (2022.01) | |
| *G06N 3/08* | (2023.01) | |
| *G06T 7/00* | (2017.01) | |
| *G16H 30/40* | (2018.01) | |
| *G16H 50/70* | (2018.01) | |

(52) U.S. Cl.
CPC .............. *A61B 90/37* (2016.02); *G06F 16/71* (2019.01); *G06F 16/7847* (2019.01); *G06N 3/08* (2013.01); *G06N 20/00* (2019.01); *G06V 10/70* (2022.01); *G09B 23/28* (2013.01); *G16H 10/60* (2018.01); *G16H 20/40* (2018.01); *G16H 30/20* (2018.01); *G06T 7/0012* (2013.01); *G06T 2207/10016* (2013.01); *G06T 2207/20081* (2013.01); *G06T 2207/30004* (2013.01); *G16H 30/40* (2018.01); *G16H 50/70* (2018.01)

(58) Field of Classification Search
CPC . G06T 2207/10016; G06T 2207/20081; G06T 2207/30004; G06T 7/0012; G06F 16/71; G06F 16/7837; G06F 16/7847; A61B 34/10; A61B 34/20; A61B 90/37
See application file for complete search history.

(56) References Cited

U.S. PATENT DOCUMENTS

| | | | |
|---|---|---|---|
| 9,532,756 | B2 | 1/2017 | Wakai et al. |
| 10,019,551 | B2 | 7/2018 | Zellner et al. |
| 2012/0069167 | A1 | 3/2012 | Liu et al. |
| 2017/0154156 | A1* | 6/2017 | Sevenster ............... G16H 10/60 |
| 2017/0213339 | A1 | 7/2017 | Hibbard et al. |
| 2018/0166167 | A1* | 6/2018 | Kanada ................. G06T 7/0012 |

OTHER PUBLICATIONS

Faria et al., "Content-based image retrieval for brain MRI: An image-searching engine and population-based analysis to utilize past clinical data for future diagnosis," NeuroImage: Clinical 7 (2015), pp. 367-376.

Huang et al., "Content-Based Image Retrieval Using Spatial Layout Information in Brain Tumor T1-Weighted Contrast-Enhanced MR Images," PLOS ONE, Jul. 2014, vol. 9, Issue 7, 13 pages.

Napel et al., "Automated Retrieval of CT Images of Liver Lesions on the Basis of Image Similarity: Method and Preliminary Results," Radiology: vol. 256, No. 1, Jul. 2010, pp. 243-252.

Okada et al., "Multi-Organ Segmentation in Abdominal CT Images," Conf. Proc. IEEE Eng. Med. Biol. Soc. 2012, 11 pages.

Schroff, F. et al., "FaceNet: A Unified Embedding for Face Recognition and Clustering", Proceedings of the IEEE Computer Society Conference on Computer Vision and Pattern Recognition 2015, Mar. 12, 2015, 10 pages.

Japanese Office Action, dated Apr. 21, 2022, in corresponding Japanese Patent Application No. 2020-545593, 2 pages.

International Search Report and Written Opinion dated Jun. 19, 2019, issued in corresponding International Application No. PCT/US2019/022352, filed Mar. 14, 2019, 18 pages.

Jiang, F., et al., "Medical Image Semantic Segmentation Based on Deep Learning," Neural Computing and Applications 29(5):1257-1265, Jul. 2017.

Litjens, G., et al., "A Survey on Deep Learning in Medical Image Analysis," Medical Image Analysis 42:60-88, Jul. 2017.

"Medical Image Computing," Wikipedia, The Free Enciclopdia, <https://en.wikipedia.org/w/index.php?title=Medical_image_computing&oldid=820670527> [retrieved Jun. 7, 2019], 19 pages.

Meyer-Bäse, A., "I. Introduction," in "Pattern Recognition in Medical Imaging," Dec. 31, 2004, Elsevier, Inc., pp. 1-13.

Surgery Theater, "Online Surgical and Medical Videos for Healthcare Professionals," specifically: "Endoscopy DU Ulcer Surgery Video—General Surgery video," Mar. 4, 2018, <http://web.archive/org/web/20180304011227/http://www.surgerytheater.com/> [retrieved Jun. 7, 2019], 2 pages.

Japanese Office Action, dated Oct. 21, 2021, in corresponding Japanese Patent Application No. 2020-545593, 5 pages.

* cited by examiner

SURGICAL VIDEO RETRIEVAL BASED ON PREOPERATIVE IMAGES

CROSS-REFERENCE TO RELATED APPLICATIONS

This application claims the benefit of U.S. Provisional Application No. 62/644,737, filed Mar. 19, 2018, which is hereby incorporated by reference in its entirety.

TECHNICAL FIELD

This disclosure relates generally to video retrieval, and in particular but not exclusively, relates to surgical techniques.

BACKGROUND INFORMATION

Study and review of past surgical cases is important in order for doctors to learn how to perform upcoming surgeries. Traditionally, doctors have been trained by observing many surgeries in-person in the operating room. This requires a lot of surgeon time (many surgeries take several hours to complete). Moreover, surgeons must be in the geographic proximity of the patient, and the type of surgery (and the type of patient) must be relevant to the future surgeries that the doctor will perform in order to adequately prepare the surgeon.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
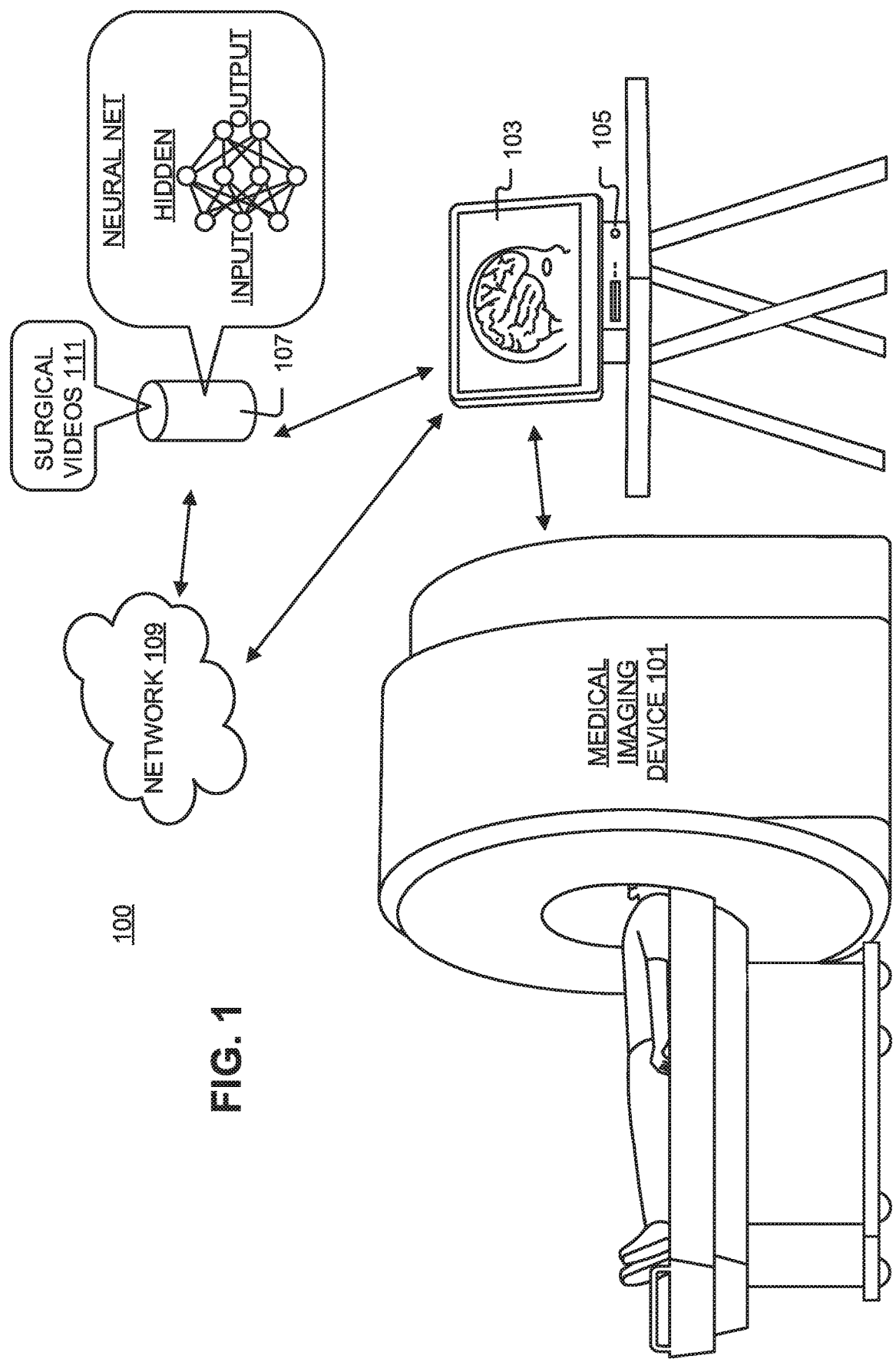
FIG. 1 illustrates a system to retrieve surgical videos, in accordance with an embodiment of the present disclosure.

Embodiments of a system and method for surgical video retrieval are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein are embodiments of a system, apparatus, and method for retrieving relevant surgical videos based, at least in part, on one or more preoperative images and/or user selected metadata. Such surgical videos may represent an important resource for preoperative planning (e.g., to help surgeons anticipate challenges and avoid potential dangers). Retrieving relevant surgical videos related to the preoperative planning may be vital, since a given procedure can vary greatly due to patient's gender, age, body shape, stage of the disease, medical history, complication, as well as numerous other potential variables. In this disclosure, we present a framework to analyze and extract features from preoperative images (e.g., magnetic resonance images, computerized tomography scans, x-ray images, positron emission technology scans, ultrasound scans, images from other medical imaging techniques, or the like) and retrieve the relevant (e.g., similar) surgical videos for an upcoming procedure to be performed on a patient based on this information.

Given (1) pairs of preoperative magnetic resonance (MR)/computerized tomography (CT) images (individual MR or CT images, or other types of images) and surgical videos from previous patients stored in a large database, and (2) MR/CT images (individually or paired, and/or other types of images) from an upcoming patient, the system here may compute the closest previous patients that have similar MR/CT images with the upcoming patient, and retrieve their surgical videos.

An array of image retrieval methods can be used to retrieve similar cases of diseases given an MR/CT image input. However, similar cases of diseases do not necessarily indicate similar surgeries. Surrounding organs, bones, and tissues may greatly affect the surgery. To address this problem, in the framework presented here, the system considers not only the similarity of diseases, but also the similarity of important surrounding regions.

In some embodiments, there are four main steps in this framework: (1) acquire organ level information (e.g., size, shape, position) from MR/CT images. The distribution of organs forms the landscape for surgeries. It should be appreciated that organ information includes information about organs, tissue, bones, cartilage and the like. (2) Acquire disease-related information (e.g., disease type, positions of lesion areas, stage of the disease) from MR/CT images or clinical data. This information establishes the region(s) of interest. (3) Compute similarity scores based on the organ distribution and disease status. In addition, a mask can be used to hide what is not relevant for a given procedure, and only organ distribution within a region of interest is used. For example if a nose cosmetic procedure is done and the image contains the eyes, there may not be a need to take the eyes into account when computing a similarity score. (4) The system retrieves surgical videos with the highest similarity scores (e.g., surgical videos within a threshold range may be selected).

In step 1, the system performs organ segmentation in MR/CT images. More specifically, a 3D fully convolutional neural network (e.g., with an input layer, one or more hidden layers, and an output layer of nodes/artificial neurons) is trained and applied to MR/CT images to segment different types of organs. A 3D deeply supervised network (3D DSN) may be used to generate a similarity score. In some embodiments, a conditional random field model may be used to enhance contour refinement. In other embodiments, multi-scale context/multi-level pyramid features and atrous convolution may be used to improve overall segmentation results. After segmentation, size, shape, and position information can be computed.

In step 2, more disease specific computation is needed. For each disease, the system is trained on, and applies, deep learning model(s) or some other method to locate the disease areas and assign disease stage. It is appreciated that "disease" broadly includes cancers, ulcers, areas of infection (bacterial or viral), dead tissue, autoimmune diseases, genetic diseases, and other types of bodily degradation or atypia. "Disease" may even include portions of unhealthy but otherwise "normal" tissue (e.g., for a gastric bypass, lap band surgery, or the like). Region of interest is then generated based on disease information and metadata about how the procedure is going to be performed (e.g., which instruments, or which style of the procedure).

In step 3, the system first filters out obvious mismatch (e.g., irrelevant) videos based on disease type, gender, age, body shape, etc. (for each type of procedure the user of the system may choose their own set of relevant parameters and have their own similarity metric). The system may then retrieve videos that have the same stage of disease and similar location of disease areas (e.g., measured by the distance of relative positions in and around organs). Finally, among these videos, the system computes the similarity between organs of two patients (e.g., similarity in size, similarity in shape, and similarity of the relative positions) inside the region of interest. The outputs of this framework are the videos with the highest similarity scores. In another embodiment, additional information (e.g., BMI, patient age, etc.) about the patient or the procedure is also used to infer similarity score. In some embodiments, the similarity score may encompass user customization and preference. For example, if there are not enough videos for one unique combination, the surgeon can choose to use fewer filters in the selection, or select videos in a particular area that the surgeon is interested in without necessarily satisfying all conditions (e.g., a surgeon can either add more criterion—be more specific—or subtracts a criterion—to find enough videos). It is further appreciated that the patient images can be scaled before a similarity score is computed (e.g., two patients are twins but one is a scaled version (taller) of the other, it would be really useful to see the video of the first patient when operating on the second patient, the fact that one is taller is less relevant). "Scaling" might mean a variety of things (e.g., shrink/enlarge vertically and/or horizontally) and for certain diseases/procedures, deformations may not even matter, only the relative positions of organs and disease do.

The following sections describe the embodiments discussed above, and additional embodiments, as they relate to the figures.

FIG. 1 illustrates a system 100 to retrieve surgical videos, in accordance with an embodiment of the present disclosure. System 100 includes medical imaging device 101, display 103, processor 105, database 107 (including surgical videos 111, and associated preoperative scans), and network 109.

As shown, medical imaging device 101 may include one of a computed tomography (CT) scan machine, a magnetic resonance imaging (MRI) machine, an X-ray machine, positron emission technology (PET) machine, ultrasound machine or the like. Display 103 may be a light emitting diode (LED) screen, liquid crystal display, projector, or the like. Processor 105 may include a localized device (e.g., included in a microcontroller, computer chip specifically designed to run machine learning algorithms such as one or more tensor processing units, a general purpose processor, distributed system running on many servers, or the like) or may include virtual machines hosted on a distributed system (e.g., network 109). Moreover, it is appreciated that some of the processing may occur locally, while other processing tasks may be performed on remote servers. Similarly, database 107 may be running locally on a hard drive or the like, or may be a distributed system running on many servers.

In the depicted embodiment, medical imaging device 101 is adapted to capture images (e.g., with x-rays, magnetic imaging, or the like) of organs in a human body and disease in a human body. It is appreciated that contrast agents may be used to highlight specific structures such as tumors in the surgical images. Display 103 is adapted to show surgical videos to a user such as a physician. Database 107 includes surgical videos and surgical scans (e.g., pre-operative MR and CT scans corresponding to each surgical video). Processor 105 is coupled (either by wires or wirelessly) to medical imaging device 101, database 107, display 103, and network 109. In the depicted embodiment, processor 105 is coupled to memory that stores instructions/logic (which may be machine code, or native instructions designed/built into the memory) that when executed by processor 105 causes system 100 to perform a variety of operations. For example, processor 105 may determine organ information including at least one of a shape of the organs, a size of the organs, or a location of the organs in the patient being imaged. Processor 105 may measure organ size, shape, and location by building a 3D reconstruction of the organs (see e.g., FIG. 2A) from the scans, and using the reconstruction, calculate data about organ volume, distance between organs (e.g., using Dice coefficient or other distance), and difference to a common reference point in the body, etc.

Similarly, processor 105 may also determine disease information/data including at least one of a shape of the disease, a location of the disease, or a stage of the disease. In some embodiments, disease shape, volume, location, and stage may similarly be determined by building a 3D reconstruction of the disease, and using the 3D reconstruction to make measurements and assess spread. It is appreciated that complex 3D model construction and associated calculations must be completed by computer systems and cannot be achieved mentally.

Using the organ and disease information, processor 105 may recall one or more of the surgical videos from database 107 based on a similarity score between the disease information and the organ information in the images captured by medical imaging device 101, and second disease information and second organ information corresponding to the surgical videos. Put another way, organ and disease information captured by imaging device 101 is compared to other organ and disease information previously captured and tagged to a specific video in database 107. For example, a pre-operative scan (e.g., MR/CT scan of a tumor) of a patient may be captured and then a video 111 of the surgery to remove the tumor may be captured. Both the pre-operative scan and the surgical video 111 may be stored in database 107. System 100 may compare images (captured by medical imaging device 101) of the current patient to preoperative images and 3D models stored in database 107. System 100 may then recall the corresponding surgical videos 111 and associated data if they are relevant to the instant patient. System 100 may then display the one or more of the surgical videos 111 on display 103.

In one embodiment, processor 105 is coupled to memory (e.g., database 107) which may include logic (either implemented in firmware, software, or a combination of the two) that includes a machine learning algorithm (e.g., a deeply supervised network). In some embodiments, the machine learning algorithm may segment the images of the organs and disease. The segmented organs and disease may be used to generate data for a 3D model of the organs and disease (see e.g., FIG. 2A). In some embodiments, the machine learning algorithm may include a plurality of deep learning models, where each deep learning model in the plurality of deep learning models is trained to recognize a different type of the disease. For example, one deep learning model may be trained to recognize melanoma in the human body, while another deep learning model is trained to recognize lymphoma. This may be used to cut down on the processing required by the machine learning algorithm since disease is often already diagnosed before a preoperative MR or CT scan is captured. In one embodiment, selecting the one or more of the surgical videos includes using metadata to calculate the similarity score. The metadata may include at least one of patient age, patient body mass index, type of disease, patient gender, or patient preexisting conditions.

In one embodiment, processor 105 may remove one or more irrelevant videos in the surgical video database from consideration by processor 105 prior to selecting one or more of the surgical videos. Put another way, a coarse filter may be applied to remove videos that have little or no relevance to the current patient. For example, a video may be irrelevant if the patient in the video has at least one of a different disease, a different gender, a different body shape, a different disease location, and/or a different age, than the first patient that is currently being examined and imaged. Irrelevant videos may be removed by using both data in the videos and metadata (e.g., age, weight, height, etc.) added to the database by the attending physician or staff.

Figure 2A:
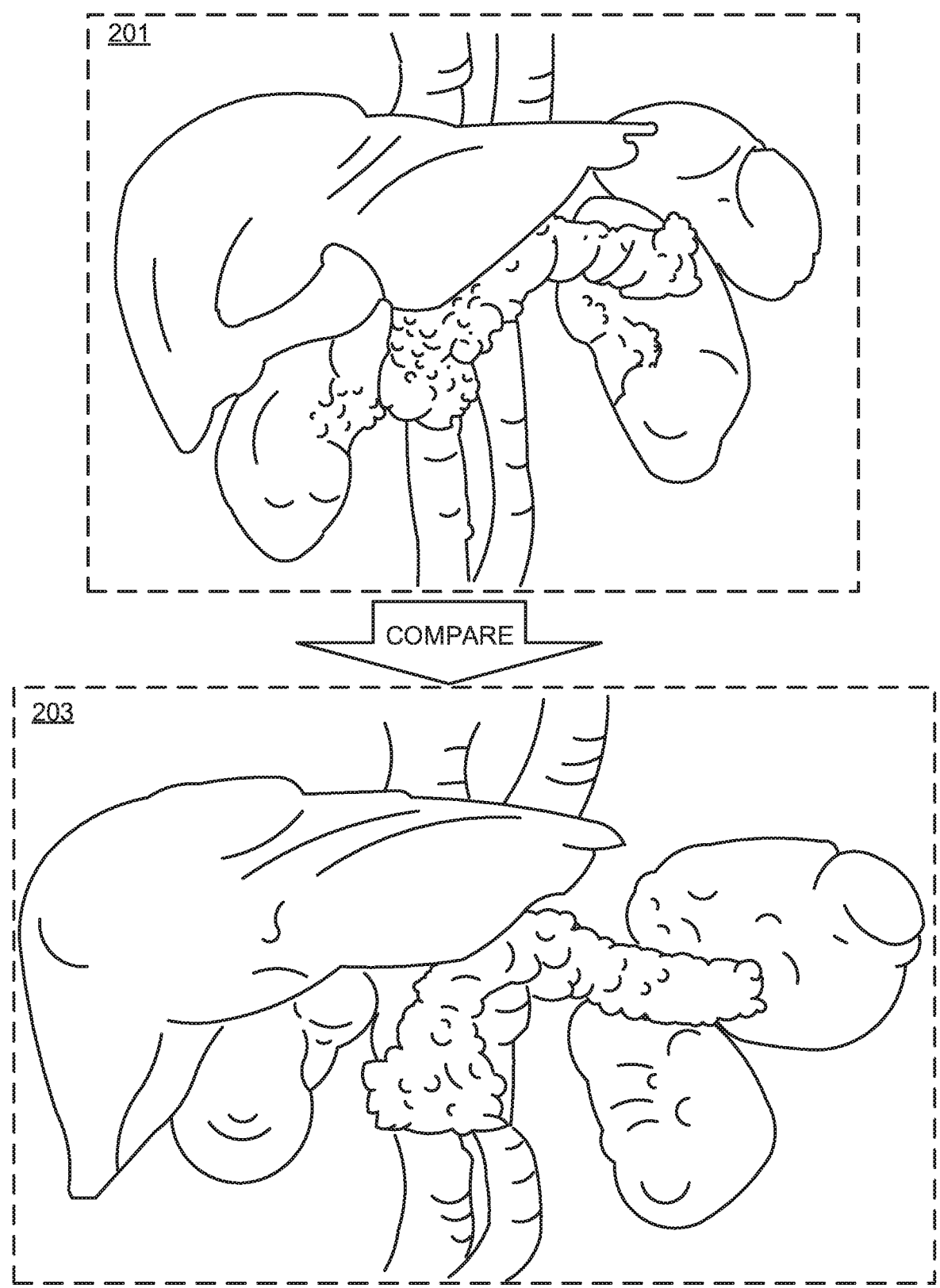
FIG. 2A illustrates organ and disease segmentation, in accordance with an embodiment of the present disclosure.

FIG. 2A illustrates organ and disease segmentation, in accordance with an embodiment of the present disclosure. As shown, the images of the organs and disease are segmented into a first 3D model 201. Using 3D model 201 the shape of the organs, the size of the organs, the location of the organs, the size/extent of disease (e.g., tumor size and spread), the shape of the disease, the location of the disease, and/or the stage of the disease may be determined. This may be compared to other preoperative images (which may be converted into 3D models 203) in the database. Preoperative images that are similar to 3D model 201 may be used to identify and pull associated surgical videos from the database.

In one embodiment a fully 3D convolutional neural network (or other type of machine learning model, algorithm, neural network, or the like) may be utilized to produce respective feature vectors associated with the preoperative images and the images or videos within a surgical video database (e.g., database 107 illustrated in FIG. 1). One or more machine learning models may be utilized for segmentation (e.g., for determining organ and/or disease information) of the preoperative images. For example, a first machine learning model may be used to identify different organs (i.e., label or otherwise annotate individual pixels as belonging to a specific organ). A second machine learning model may receive the output (e.g., the annotated images) to produce a feature vector characterizing the image (e.g., each organ may have an associated feature vector and/or a feature vector may characterize the image as a whole). Specifically, since many medical imaging techniques produce 3-dimensional images or representations (e.g., CT scans, MRI scans, and the like), a fully 3D convolutional neural network may receive inputs for each pixel of the image related to relative x, y, and z position within the 3-dimension space of the image as well as one or more color values (e.g., for grayscale and/or color images) and outputs a feature vector which describes or otherwise characterizes the images. Thus each of the preoperative images (e.g., of a patient in which a procedure is to be performed on) as well as images (preoperative or otherwise) from a database may be characterized in a comparable manner. It is appreciated that in some embodiments, still images from videos may be utilized for determining feature vectors.

Figure 2B:
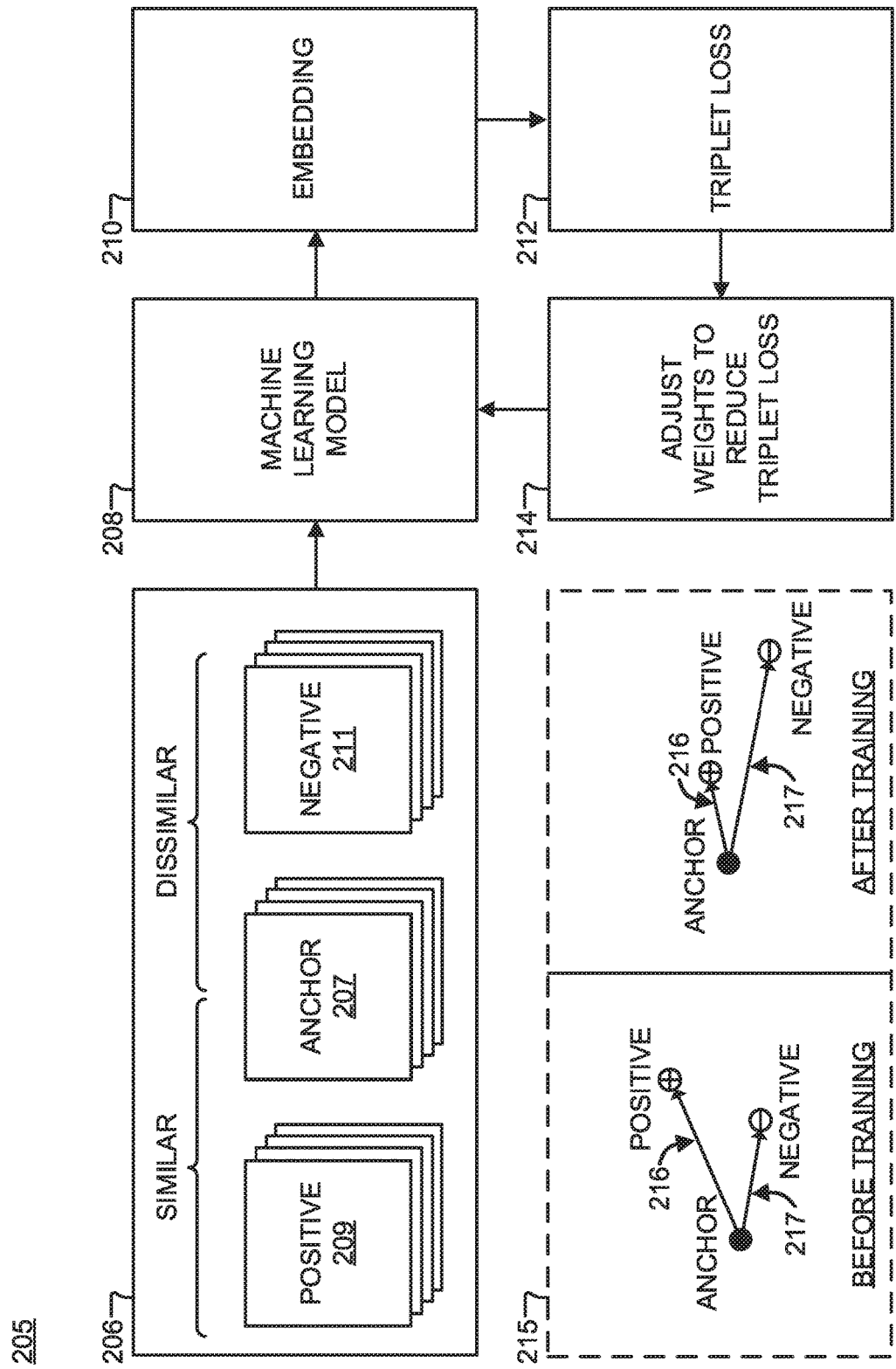
FIG. 2B illustrates an example flow chart for training a machine learning model to provide an image similarity score, in accordance with an embodiment of the present disclosure.

FIG. 2B illustrates an example flow chart 205 for training a machine learning model 208 (e.g., a 3D deeply supervised network) to provide an image similarity score, in accordance with an embodiment of the present disclosure. It is appreciated that flow chart 205 is one possible implementation of training a machine learning model to provide an image similarity score and that there may be other training methods and/or variance of machine learning model architectures that may be applied to provide an image similarity score, in accordance with the embodiments of the present disclosure. Additionally, it is appreciated that blocks may be added to, or removed from, flock chart 205 in accordance with the teachings of the present disclosure.

Block 206 illustrates providing training data including a plurality of surgical images and/or videos. The training data may come from a surgical video database including preoperative images, surgical videos, or the like. Training data may be annotated (e.g., by a doctor, surgeon, medical practitioner, other individuals, and/or one or more machine learning models). Specifically, within the training data triplets of example images are collated. Within each triplet of images there is an anchor image, a positive image, and a negative image. These images may be 2D images, 3D images, videos, and the like and may include color data, grayscale data, or otherwise. Each of the anchor images 207 is matched with a similar image (e.g., positive image 209) and a dissimilar image (e.g., negative image 211). The triplet set of images may be selected (e.g., by a doctor, surgeon, other individual, or otherwise) from annotated or labeled preoperative images (e.g., by a doctor, surgeon, or other individual), unlabeled preoperative images, and/or other images, videos, and the like from a database (e.g., surgical video database as illustrated in FIG. 1). In some embodiments, the similar images (i.e., positive and anchor image pair) are selected from the same patient at different time periods. In the same or other embodiments, images are gathered via various data collecting methods (e.g., comparing metadata to remove irrelevant images and then selecting from the relevant images suitable similar and dissimilar images).

Each triplet of images (or batches of the training data including at least one of the triplet of images) are passed to a machine learning model as indicated in block 208. The machine learning model is trained to embed (e.g., encode) images into a feature space, which the square (or absolute value of) distance within the feature space between images corresponds to similarity (or lack thereof). The machine learning model may be one or more convolutional neural networks, each including a plurality of interconnected nodes arranged in layers to form the architecture of the deep neural network. As illustrated in block 210, images that pass through the machine learning model are subsequently embedded within the feature space.

Once the triplet set of images is embedded within the feature space, block 210 proceeds to block 212 in which a loss value is determined from a loss function that is indicative of a triplet loss. In other words, the loss function is defined to involve the triplet set of images. Specifically, the loss function is defined such that a predetermined margin (i.e., distance of separation) within the feature space is enforced between similar and dissimilar pairs of images as illustrated in block 215. Once the loss value is known, block 212 proceeds to block 214 in which an optimization algorithm (e.g., gradient descent) is used to adjust or otherwise update the weights of the machine learning model to reduce the triplet loss. This is an iterative process in which the machine learning model has weights updated for each of the triplet set of images until training is completed.

Block 215 shows an exemplary triplet set of images within the feature space before and after training of the machine learning model. Before training, within the feature space, a first distance 216 between the anchor and positive image is greater than a second distance 217 between the anchor and the negative image. However, after training, a margin is enforced between positive and negative pairs such that the first distance 216 is less than the second distance 217. In this way, the distance within the feature space between images is indicative of similarity (or lack thereof).

Accordingly, the trained machine learning model may be used to embed an input image (e.g., a preoperative image that a surgeon would like to find comparable images associated with surgical videos) within the feature space. Subsequently, the separation distance between the input image and other images within the feature space may be utilized to cull or otherwise retrieve related surgical videos. For example, all images within a pre-determined threshold value of separation distance (squared or otherwise) may be retrieved. In the same or other embodiments, the position within the feature space may be one of many feature vectors to be utilized in determining a similarity score. In some embodiments, the separation distance (or variant thereof) may itself correspond to the similarity score.

Figure 2C:
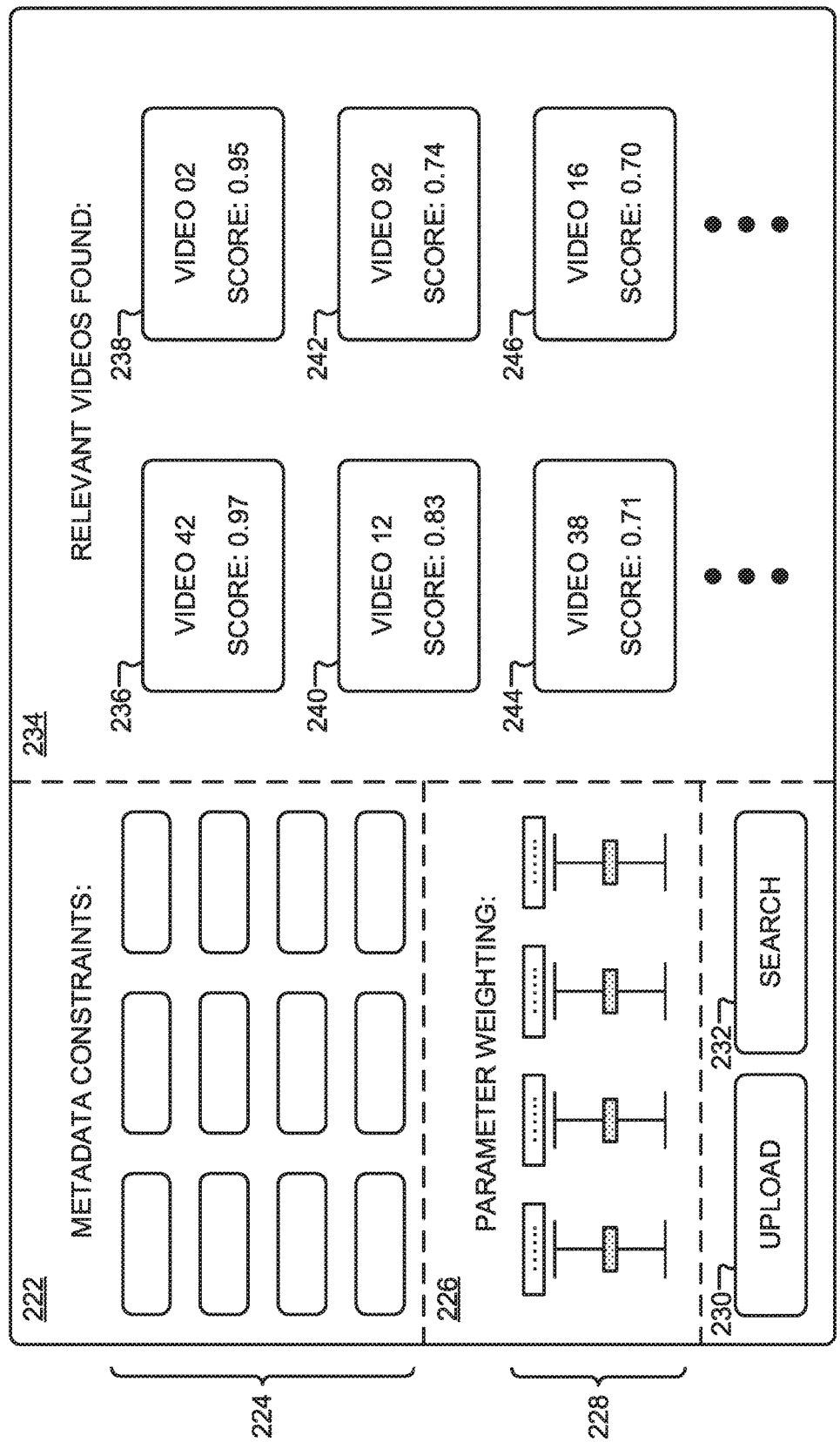
FIG. 2C illustrates an example graphical user interface output to a display for retrieving relevant surgical videos based on one or more preoperative images, in accordance with an embodiment of the present disclosure.

FIG. 2C illustrates an example graphical user interface (GUI) 220 output to a display (e.g., display 103 illustrated in FIG. 1) for retrieving relevant surgical videos based, at least in part, on one or more preoperative images, in accordance with an embodiment of the present disclosure. GUI 220 provides an exemplary interface that a user (e.g., surgeon, engineer, or otherwise) may utilize in accordance with the embodiments of the disclosure to provide inputs (e.g., constraints, parameter weighting, preoperative image selection, and the like) that may be utilized by a system (e.g., system 100 illustrated in FIG. 1) to retrieve and output (relevant) surgical videos. It is appreciated that GUI 220 is merely demonstrative and should not be deemed limiting. Rather, GUI 220 may be configurable dependent on a variety of factors (e.g., user selection, type of procedure, and the like). Thus it is appreciated that other implementations of graphical user interfaces may be utilized, in accordance with the teachings of the present disclosure.

GUI 220 includes various sections to display information and/or interact with a user of the system. In the illustrated embodiment, the sections include a constraint section 222, a parameter weighting section 226, a retrieved video section 234, as well as upload 230 and search 232 buttons. Constraint section 222 includes a plurality of constraints 224 that may be configured for filtering of surgical videos within a database (e.g., database 107 illustrated in FIG. 1). In other words, the user may filter videos deemed to be irrelevant to provide potentially reduced computational burden, increased accuracy/relevancy of retrieved videos. In some embodiments, the plurality of constraints 224 may include metadata (e.g., patient age, patient body mass index, type of disease, patient gender, patient preexisting conditions, among others) that may be associated with surgical videos in a surgical video database. For example, a user may adjust one of the plurality of constraints 224 to filter out patients by gender (e.g., if the individual to have a surgical procedure is a male, only videos of males are searched). In the same or other embodiments, constraints may be filtered by range. For example, one of the plurality of constraints 224 may enable a user to filter out surgical videos outside of a threshold range (e.g., if a user of the system decides only surgical videos of individuals between 18 years and 24 years of age should be considered relevant, videos outsight of the threshold range will be filtered out).

Parameter weighting section 226 includes a plurality of parameters 228, which may be ranked, or otherwise weighted by a user of the system to indicate relevancy. Parameters may include any of the previously discussed metadata (e.g., patient age, patient body mass index, type of disease, patient gender, or patient preexisting conditions), organ specific parameters (e.g., size, shape, position), disease specific information (e.g., at least one of a shape of the disease, a location of the disease, or a stage of the disease). It is appreciated that any one of, combination of, but not necessarily all of, the parameters may be individually ranked. In some embodiments, parameters are ranked according to a priority level (e.g., a first and second parameter 228 is ranked level 1 to indicate high priority, a third and fourth parameter is ranked level 2 to indicate medium priority, and a fifth parameter is ranked level 3 to indicate low priority). In some embodiments, parameters are ranked based on an absolute scale (e.g., the sum total of rank for all parameters equals 1). In the same or other embodiments, a machine learning model is trained to rank parameters in addition to, or in lieu of, manual ranking by the user of the system. For example, a user may upload (e.g., via button 230) preoperative images with associated metadata, organ information, and/or disease information of a patient (e.g., a preoperative patient that a surgeon would like to retrieve relevant surgical videos). A machine learning model may subsequently pre-select metadata constraints and/or parameter weighting values based on the uploaded content. Then, if desired, the user may adjust the pre-selected values (e.g., the surgeon may find based on experience that a particular parameter or constraint is particularly important or relevant).

Once preoperative images have been uploaded or selected from a database and the metadata constraints and/or parameter weighting values have been configured, a user of the system may search for relevant videos by selecting button 232. Accordingly, relevant videos found section 234 may be populated after a search is performed and relevant surgical videos based on a similarity score are retried and displayed. Surgical videos may be retrieved from a database (e.g., database 107 illustrated in FIG. 1). Based on at least one of organ information or disease information associated with preoperative images (e.g., of a patient a surgeon would like to obtain related videos as part of preparation of an upcoming procedure), a plurality of surgical videos (e.g., videos 236-246) may be displayed. Each of the plurality of surgical videos may be indexed (e.g., within the database) compared to the preoperative images that were uploaded/selected by the user to compute respective similarity scores. In the illustrated embodiments, the similarity score is a value between 0 and 1, with a score of 1 corresponding to perfect relation (i.e., only the same surgical video compared to itself should result in a perfect relation) and 0 corresponding to irrelevant. In some embodiments, the retrieved surgical videos will be displayed according to their relative rank in terms of similarity score (e.g., the surgical videos are displayed in descending order from highest score to lowest score). In the same or other embodiments, there may be a threshold similarity score value or range, in which videos outside of the value or range will not be displayed (e.g., only surgical videos with a similarity score of greater than 0.6 may be retrieved).

Figure 2D:
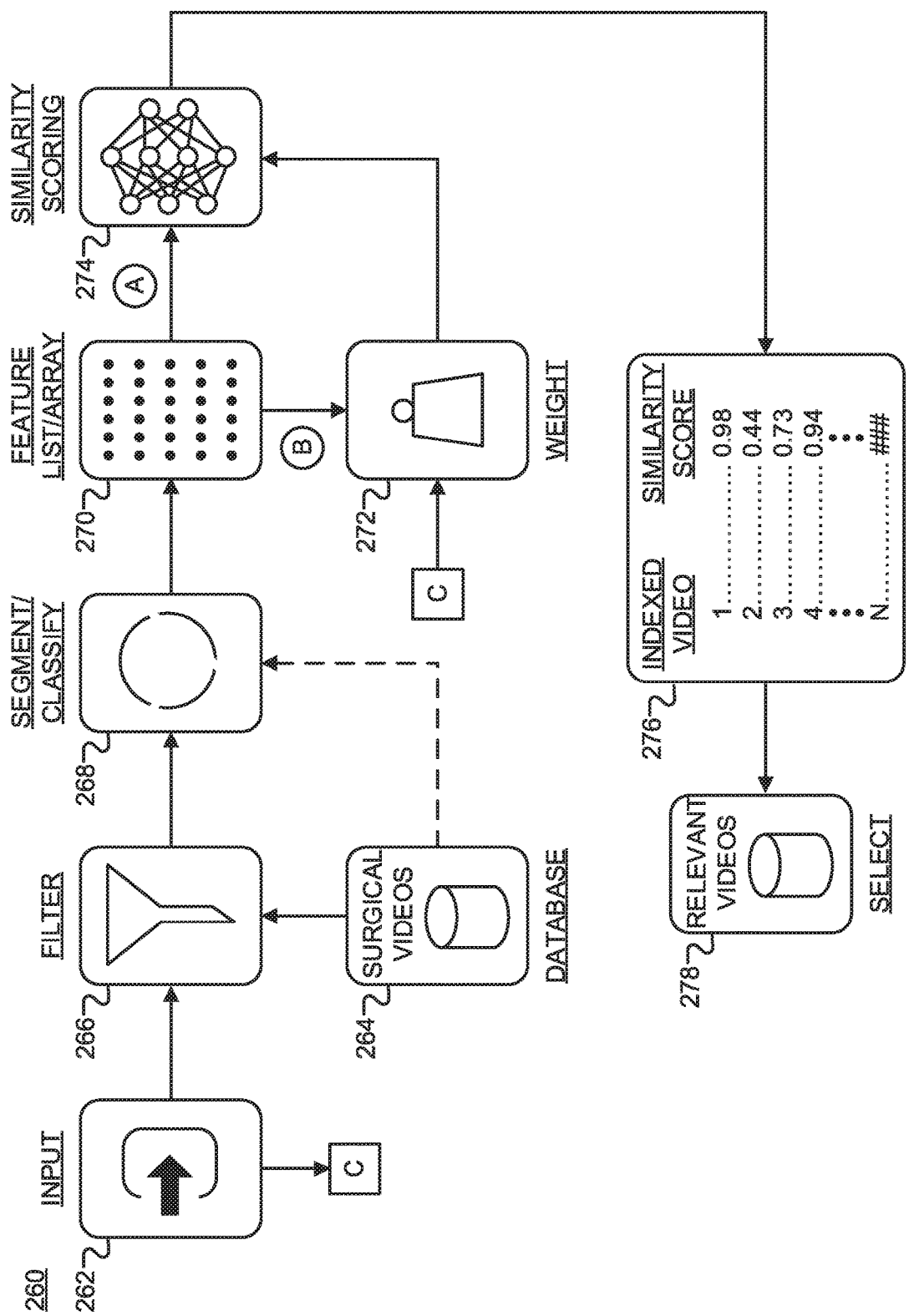
FIG. 2D illustrates a flow chart to retrieve surgical videos based on one or more preoperative images, in accordance with an embodiment of the present disclosure.

FIG. 2D illustrates a flow chart 260 to retrieve surgical videos based, at least in part, on one or more preoperative images, in accordance with an embodiment of the present disclosure. Flow chart 260 is one possible implementation a system (e.g., system 100 illustrated in FIG. 1) may use to calculate a similarity score between one or more preoperative images (e.g., organ information, disease information, among other information related to a patient) and surgical videos (e.g., with associated organ information, disease information, or otherwise) to retrieve relevant surgical videos indexed to the database. In one embodiment, flow chart 260 corresponds to a system level architecture that is complemented by GUI 220 illustrated in FIG. 2C. It is appreciated that numbered blocks 262-278 may occur in any order and even in parallel. Additionally, blocks may be added to, or removed from, flow chart 260 in accordance with the teachings of the present disclosure.

As illustrated in FIG. 2D, block 262 illustrates receiving input information (e.g., metadata constraints, parameter weighting values, and preoperative images from a database or otherwise). For example, in one embodiment, the preoperative images may be associated with first organ information (e.g., at least one of a shape of the organs, a size of the organs, a location of the organs, or otherwise) and first disease information (e.g., at least one of a shape of the disease, a location of the disease, a size of the disease, a stage of the disease, or otherwise). In other embodiments, the first organ information and first disease information may not be known initial, but may subsequently become known (e.g., as determined by block 268).

Block 266 shows filtering a plurality of videos from a database including a plurality of surgical videos. In other words, based on the inputs (e.g., metadata constraints, parameter weighting values, or the like) surgical videos deemed irrelevant may be filtered by block 266 such that not every video indexed within the database 264 is passed to block 268.

Block 268 illustrates segmenting and/or classifying surgical videos to generate a feature vector associated with the preoperative images, surgical videos, and the like. Surgical videos from database 264 may be passed to block 268 based on information received from block 266 (e.g., surgical videos having metadata outside of a threshold range are not passed to block 268). Block 268 subsequently classified each of the preoperative images, surgical videos, and the like that are passed to it and outputs an associated feature vector. For example, if the preoperative images are not annotated, block 268 may determine a feature vector that includes the first organ information, which may be indicative of at least one of a shape of the organs, a size of the organs, or a location of the organs.

Individual organs may be segmented from the preoperative images and a size, shape, or other characteristic value determined. In some embodiments a machine learning model (e.g., fully 3D convolutional neural network, other neural network, or other machine learning model architectures) may be utilized to determine the organ information and output to a feature vector associated with the corresponding image. Additionally, disease information may also be determined (e.g., a shape of the disease, a location of the disease, a size of the disease, a stage of the disease, or otherwise) via a machine learning model that characterizes or otherwise classifies the disease information (e.g., based on the segmentation). In one embodiment, a machine learning model trained to classify diseases based on a preoperative image input may be utilized to provide the disease information. In the same or other embodiments, the preoperative images may already having organ information and/or disease information segmented/classified (i.e., annotated). In such an embodiment, block 268 may generate a feature vector based on the annotated information. In some embodiments, organ or disease information may further include comparable attributes (e.g., 3D shape, texture, roughness, size, location of the images of organs and/or disease).

In one embodiment, block 268 includes a 3D deeply supervised network that generates an image similarity score (e.g., as described previously in relation to FIG. 2B) between the input preoperative images and the images or videos (or portions thereof) within a surgical video database (e.g., before or after filtering in block 266). The machine learning model places the input preoperative images within the same feature space (i.e., embedding) as the other images or videos (from the surgical video database) such that the squared distance (or otherwise) between pairs of images (e.g., an input preoperative image and an image from the surgical video database) corresponds to an image similarity score. A feature vector or vectors may then be assigned to the squared distance between image pairs, which may be one of many different feature vectors for retrieving related surgical images/videos.

In some embodiments, the feature vectors generated by block 268 may have no tangible descriptors. Rather, the machine learning model may use feature engineering to determine which features of the preoperative images are relevant. Such relevant features may not have a descriptor that can be accurately described. Thus, while each feature vector may include elements that are describable (e.g., organ information such as a shape, size, or location of organs, disease information such as a shape, location, size, or stage of disease), other features may also be included. Thus, each feature vector for each of the preoperative images may include tens, hundreds, thousands, or more based, for example, on the architecture of the machine learning model.

Block 270 receives each feature vector associated with each of the preoperative images (e.g., first organ information from the images of organs, first disease information from the images of disease, second disease information indexed to surgical videos, second organ information indexed to surgical videos) and assembles a feature list or array. In one embodiment, each feature vector is concatenated to form a feature array. In one embodiment, each row of the feature array may correspond to an individual image (e.g., preoperative image, surgical video, or the like). In the same or other embodiment, each element of the feature vector may be standardized such that a column of the feature array corresponds to the same feature (e.g., size, shape, location of organ, volume of organ, size of disease, shape of disease, location of disease, stage of disease, texture of organ, texture of disease, roughness of organ, roughness of disease, or other features such as those determined via feature engineering).

In some embodiments, block 270 proceeds through route A to block 274 in which similarity scoring occurs. Specifically, one or more machine learning models are trained to compare an input feature vector (e.g., related to first organ information, first disease information, or other features of an image from a surgical video or otherwise). The machine learning model then compares the input feature vector to the feature list/array to output a similarity score for each feature vector (e.g., associated with a respective surgical video indexed to a database) within the feature list/array. In some embodiments, the similarity score may be a confidence value that the machine learning model outputs when comparing images.

In one embodiment, the similarity score is determined based on a statistical comparison between feature elements within a vector. For example, a feature vector of a first preoperative image includes organ information, including a first element associated with organ size, and disease information, including a second element associated with disease shape. A second feature vector (e.g., from the feature list/array) is associated with a first surgical video included in a database. The second feature vector includes second organ information, including a first element associated with organ size and second disease information, including a second element associated with disease shape. Values of respective elements may be normalized and subsequently compared. The difference between individual elements (e.g., difference between first elements of the first and second feature vector). The differences between elements may subsequently be squared and summed (e.g., root mean square) to determine the similarity score for the first surgical video indexed in the database. This process may be repeated for each of the feature vectors within the feature list/array.

In some embodiments a specified feature vector from the feature list/array may be utilized to determine the similarity score. For example, in one embodiment images or videos are filtered from the surgical video database based on metadata (e.g., as explained for block 266). Subsequently, an image similarity score (e.g., as described in relation to FIG. 2B) is determined between pairs of images via a machine learning model. In such embodiments, the similarity score may thus correspond to the squared distance (or otherwise) within the feature space embedding between the preoperative image(s) and other images or videos from the surgical video database. In one embodiment, the squared distance may be normalized.

In the same or other embodiments, block 270 may proceed to block 272, in which individual features (i.e., elements of the feature vectors) are ranked (e.g., according to the input parameter weighting and/or as determined via a machine learning model). Thus, individual elements of the feature list/array may be normalized and subsequently weighted. For example, in one embodiment, each element within a row of the feature list/array is associated with a particular feature or parameter (e.g., disease information, organ information, etc.). Parameters may be weighted via a row of coefficients that is commonly associated with each of the feature vectors, such that specific elements/features are weighted in the same way (e.g., if a size of organ is weighted, it will be equally weighted across all feature vectors). In other words, when block 272 proceeds to block 274, a weighted average of the feature elements may be utilized to determine the similarity score, in accordance with the teachings of the disclosure.

Once the similarity score for each of the feature vectors included in the feature list/array is known, block 274 proceeded to block 276, which determined which surgical videos in the database are indexed to which feature vector in order to associate respective surgical videos with the corresponding similarity score. For example, block 276 illustrates indexed video 1 having a similarity score of 0.98, indexed video 2 having a similarity score of 0.44, and so on.

Block 276 proceeds to block 278, which retrieved relevant surgical videos. In particular, the relevancy of the surgical videos within the database may be determined and retrieved based on their similarity score in relation to a threshold value or range. In the embodiment, the threshold range for relevancy corresponds to any value greater than 0.7. Thus, in the illustrated embodiment, block 278 would select (and display) a list of surgical videos from the database having a similarity score above 0.7 (e.g., indexed videos 1, 3, and 4).

Figure 3:
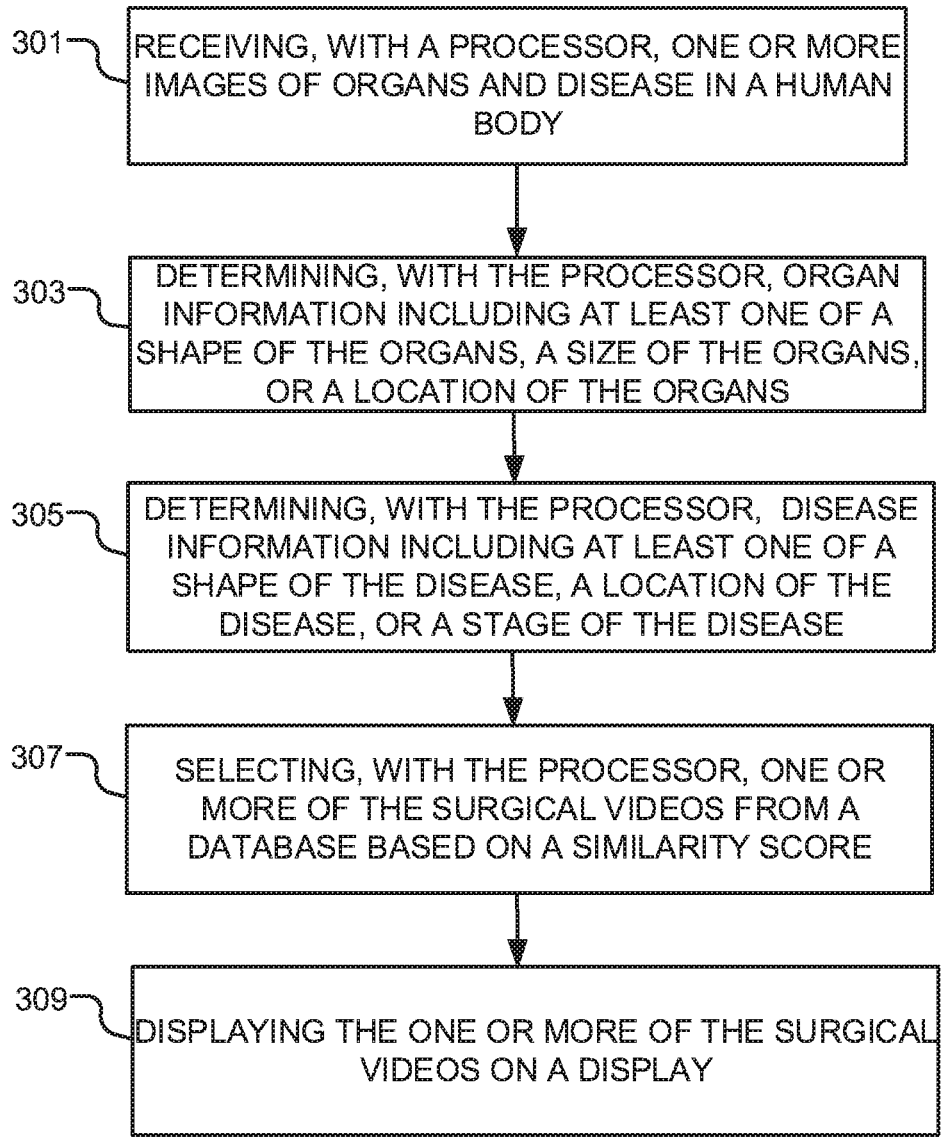
FIG. 3 illustrates a method to retrieve surgical videos, in accordance with an embodiment of the present disclosure.

FIG. 3 illustrates a method to retrieve surgical videos, in accordance with an embodiment of the present disclosure. It is appreciated that numbered blocks 301-309 may occur in any order and even in parallel. Additionally, blocks may be added to, or removed from, method 300 in accordance with the teachings of the present disclosure.

Block 301 shows receiving, with a processor, data including one or more images of organs and disease in a human body. In some embodiments, the one or more images of the organs and disease were captured with a medical imaging device such as one of a computed tomography (CT) scan machine, a magnetic resonance (MR) imaging machine, or an X-ray machine. It is appreciated that the images may be captured by the medical imaging device (and stored in a database) prior to beginning method 300. Put another way, the device running method 300 may not have direct communication with a medical imaging device.

Block 303 depicts determining, with the processor, organ information including at least one of a shape of the organs, a size of the organs, or a location of the organs from the image data. In some embodiments, the processor has logic including a machine learning algorithm, and determining the organ information includes segmenting the images of the organs using the machine learning algorithm. In some embodiments, the machine learning algorithm includes a convolutional neural network (CNN) and/or a deeply supervised network. In one embodiment, the machine learning algorithm may include an input layer, one or more hidden layers, and an output layer. Thus embodiments of the method presented here use machine intelligence to analyze human data.

Block 305 illustrates determining, with the processor, disease information including at least one of a shape of the disease, a location of the disease, or a stage of the disease. Determining disease information may be achieved in a similar manner to how organ information is determined. It is appreciated that the machine learning algorithm may include a plurality of deep learning models, where each deep learning model in the plurality of deep learning models is trained to recognize a different type of disease. For example, one deep learning model may be trained to recognize melanoma from surrounding tissue, another deep learning model may be trained to recognize brain cancer from surrounding tissue, etc. Supplying the algorithm with the type of disease may be useful to more accurately segment (e.g., parse what is healthy from what is unhealthy) disease and healthy tissue in preoperative scans, since initial diagnosis of a specific disease is typically performed manually, and since it removes a layer of computational complexity (determining the type of the disease) from the calculations of the machine learning algorithm.

Block 307 shows selecting, with the processor, one or more of the surgical videos from a database based on a similarity score (e.g., difference in volume, difference in surface area, root mean square of several of the variables listed herein, weighted score using arbitrary units, or the like) between the disease information and the first organ information in the images, and first second disease information and second organ information corresponding to the surgical videos. It is appreciated that in some embodiments, each of the surgical videos in the database has at least one associated pre-operative image stored in the database, and the second disease information and the second organ information are derived from the at least one associated pre-operative image. For example, prior to a patient having surgery, the patient may receive an MR or CT scan to show the location of disease or damage, then the patient could have surgery which is recorded in video format. Both the pre-operative MR/CT scan and the video recording of the surgery may be uploaded to the database and indexed to each other. Accordingly, the machine learning algorithm presented here may search the preoperative scans to find similar surgical videos. This is because the similarity of organs and disease may not necessarily be visible in the video. For example, the surgery may be performed arthroscopically, and the video camera may not see the full extent of the disease.

In some embodiments, selecting the one or more of the surgical videos includes using metadata to calculate the similarity score. The metadata may include at least one of patient age, patient body mass index, type of disease, patient gender, or patient preexisting conditions. This data may be added by a doctor when the video and preoperative scans are uploaded to the database. In some embodiments, metadata may be used to remove one or more irrelevant videos in the surgical videos from consideration by the processor, prior to the processor selecting one or more of the surgical videos. Put another way, the processor may screen out clearly irrelevant videos from the pool of videos being recalled. For example, if one video in the database is tagged as "tonsillectomy" and the doctor is looking for surgical videos related to excising melanoma, the tonsillectomy will not be considered. Put more generally, the processor may deem one or more videos "irrelevant" if the patient in the video has a different disease, a different gender, a different body shape, a different disease location, or a different age, than the first patient that needs the operation.

Similar to how videos of patients with irrelevant conditions may be excluded from consideration, videos about disease in other parts of the body may also be filtered out. In one embodiment, similarity score is calculated using the organ information and disease information within a region of interest, where the region of interest is a volume within the human body. Put another way, if the patient at hand has disease in her abdomen, videos of brain surgery may be excluded, because in this embodiment, the region of interest is the patient's abdomen. Using these coarse filtering techniques (e.g., using metadata and regions of interest to only focus on the most relevant videos in the database), the processing time may be drastically reduced since the machine learning algorithm only needs to process a small percentage of the 3D image data in the database.

Block 309 depicts displaying the one or more of the surgical videos on a display. This may include sending the surgical videos that were recalled from the database to a display. The user may select the number of videos they would like retrieved; this way the system may only return the most relevant videos. The retrieved videos could be shown as thumbnails. Under the thumbnail there could be a short description of the contents of the video (e.g., type of disease the patient in the video has, the age of the patient in the video, the gender of the patient in the video, the body mass index of the patient in the video, the location of the disease, or the like). This description may also be used as metadata to sort and compare videos.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system, comprising:
a database including surgical videos; and a controller including a processor coupled to memory and the database, wherein the memory stores information that when executed by the processor causes the system to perform operations including:
receiving, with the processor, one or more input preoperative images of organs and disease in a human body obtained from a medical imaging device;
determining, with the processor, first organ information and first disease information from the one or more input preoperative images using a machine learning algorithm included in the memory to generate a feature vector associated with the one or more input preoperative images, wherein the first organ information includes at least one of a shape of the organs, a size of the organs, or a location of the organs, and wherein the first disease information includes at least one of a shape of the disease, a location of the disease, a size of the disease, or a stage of the disease, and wherein the feature vector includes the first organ information and the first disease information;

calculating, with the processor, a similarity score between the one or more input preoperative images and the surgical videos included in the database, wherein the similarity score corresponds to a comparison between the feature vector associated with the one or more input preoperative images and corresponding feature vectors associated with second disease information and second organ information indexed to the surgical videos;

selecting, with the processor, one or more of the surgical videos based on the similarity score for display;

inputting the one or more input preoperative images into the machine learning algorithm to determine a position of the one or more input preoperative images within a feature space, wherein the feature vector includes the position; and determining a distance from the position of the one or more input preoperative images within the feature space to corresponding positions within the feature space for surgical videos included in the database when calculating the similarity score, wherein the similarity score is based, at least in part, on the distance.

2. The system of claim 1, wherein the medical imaging device includes one of a computed tomography (CT) scan machine, a magnetic resonance imaging (MM) machine, ultrasound machine, positron emission tomography (PET) machine, or an X-ray machine.

3. The system of claim 1, wherein determining the first organ information includes segmenting the organs from the one or more input preoperative images using the machine learning algorithm.

4. The system of claim 3, wherein the machine learning algorithm is trained via a triplet loss method for determining the similarity score.

5. The system of claim 1, wherein the machine learning algorithm includes a plurality of deep learning models, each trained to recognize one or more different types of diseases, and wherein at least one of the plurality of deep learning models is trained to recognize the disease associated with the first disease information.

6. The system of claim 1, wherein the memory further stores information that when executed by the processor causes the system to perform operations including:

removing one or more irrelevant videos in the surgical videos from consideration by the processor prior to the processor selecting the one or more of the surgical videos.

7. The system of claim 6, wherein the one or more irrelevant videos depict at least one of a different disease, a different gender of patient, a different body shape of patient, a different disease location, or a different age of patient, than a patient shown in the one or more input preoperative images of the organs and the disease.

8. The system of claim 1, wherein calculating the similarity score includes using metadata including at least one of patient age, patient body mass index, type of disease, patient gender, or patient preexisting conditions.

9. The system of claim 1, wherein the each of the surgical videos in the database has at least one associated preoperative image stored in the database, and wherein the second disease information and the second organ information are derived from the at least one associated preoperative image, and wherein the at least one preoperative image includes at least one of a computed tomography (CT) scan, a magnetic resonance imaging (MRI) scan, ultrasound image, positron emission tomography scan, or an X-ray.

10. The system of claim 1, wherein the memory further stores information that when executed by the processor causes the system to perform operations including:

weighting positionally common elements included in the feature vector associated with the one or more input preoperative images and the corresponding feature vectors associated with the second disease information and second organ information via predetermined coefficients when generating the comparison.

11. The system of claim 1, wherein the one or more of the surgical videos selected correspond to a subset of the surgical videos, the similarity score for the one or more input preoperative images to each of the one or more surgical videos being greater than a threshold value.

12. A method for the retrieval of surgical videos, comprising:

receiving, with a processor coupled to memory and a database, one or more input preoperative images of organs and disease in a human body, wherein the one or more input preoperative images of the organs and the disease were captured with a medical imaging device, and wherein the database includes surgical videos;

determining, with the processor, first organ information and first disease information from the one or more input preoperative images using a machine learning algorithm included in the memory to generate a feature vector associated with the one or more input preoperative images, wherein the first organ information includes at least one of a shape of the organs, a size of the organs, or a location of the organs, and wherein the first disease information includes at least one of a shape of the disease, a location of the disease, a size of the disease, or a stage of the disease, and wherein the feature vector includes the first organ information and the first disease information;

calculating, with the processor, a similarity score between the one or more input preoperative images and the surgical videos included in the database, wherein the similarity score corresponds to a comparison between the feature vector associated with the one or more input preoperative images and corresponding feature vectors associated with second disease information and second organ information indexed to the surgical videos;

selecting, with the processor, one or more of the surgical videos from the database based on the similarity score for display;

inputting the one or more input preoperative images into the machine learning algorithm to determine a position of the one or more input preoperative images within a feature space, wherein the feature vector includes the position; and determining a distance from the position of the one or more input preoperative images within the feature space to corresponding positions within the feature space for surgical videos included in the database when calculating the similarity score, wherein the similarity score is based, at least in part, on the distance.

13. The method of claim 12, wherein the surgical videos in the database each has at least one associated preoperative image stored in the database, and wherein the second disease information and the second organ information are derived from the at least one associated preoperative image.

14. The method of claim 12, wherein determining the first organ information includes segmenting the organs from the one or more input preoperative images using the machine learning algorithm.

15. The method of claim 12, wherein the machine learning algorithm includes a plurality of deep learning models, each trained to recognize one or more different types of diseases, and wherein at least one of the plurality of deep learning models is trained to recognize the disease associated with the first disease information.

16. The method of claim 12, wherein calculating the similarity score includes using metadata including at least one of patient age, patient body mass index, type of disease, patient gender, or patient preexisting conditions.

17. The method of claim 12, wherein calculating the similarity score includes using the first organ information and the first disease information within a region of interest, wherein the region of interest is a volume within the human body.

18. The method of claim 12, wherein the medical imaging device includes one of a computed tomography (CT) scan machine, a magnetic resonance imaging (MM) machine, ultrasound machine, positron emission tomography (PET) machine, or an X-ray machine.

19. A non-transitory computer-readable medium with instructions stored thereon that cause a computing system to perform operations comprising:

receiving, with the computing system, one or more input preoperative images of organs and disease in a human body, wherein the one or more input preoperative images of the organs and the disease were captured with a medical imaging device and stored in a database, wherein the database includes surgical videos;

determining, with the computing system, first organ information and first disease information from the one or more input preoperative images using a machine learning algorithm to generate a feature vector associated with the one or more input preoperative images, wherein the first organ information includes at least one of a shape of the organs, a size of the organs, or a location of the organs, and wherein the first disease information includes at least one of a shape of the disease, a location of the disease, or a stage of the disease, and wherein the feature vector includes the first organ information and the first disease information;

calculating, with the computing system, a similarity score between the one or more input preoperative images and the surgical videos included in the database, wherein the similarity score corresponds to a comparison between the feature vector associated with the one or more input preoperative images and corresponding feature vectors associated with second disease information and second organ information indexed to the surgical videos;

selecting, with the computing system, one or more of the surgical videos from the database based on the similarity score for display;

inputting the one or more input preoperative images into the machine learning algorithm to determine a position of the one or more input preoperative images within a feature space, wherein the feature vector includes the position; and determining a distance from the position of the one or more input preoperative images within the feature space to corresponding positions within the feature space for surgical videos included in the database when calculating the similarity score, wherein the similarity score is based, at least in part, on the distance.

20. The non-transitory computer readable medium of claim 19, wherein determining the organ information includes segmenting the organs from the one or more input preoperative images using the segmenting machine learning algorithm.

21. The non-transitory computer readable medium of claim 19, wherein calculating the similarity score includes using metadata, wherein the metadata includes at least one of patient age, patient body mass index, type of disease, patient gender, or patient preexisting conditions.

22. The non-transitory computer readable medium of claim 19, wherein the medical imaging device includes one of a computed tomography (CT) scan machine, a magnetic resonance imaging (MM) machine, ultrasound machine, positron emission tomography (PET) machine, or an X-ray machine.

23. The non-transitory computer readable medium of claim 19, wherein the surgical videos in the database each has at least one associated preoperative image stored in the database, and wherein the second disease information and the second organ information are derived from the at least one associated preoperative image.

* * * * *